(12) United States Patent
Lange et al.

(10) Patent No.: US 7,498,348 B2
(45) Date of Patent: Mar. 3, 2009

(54) 1 H-IMIDAZOLE DERIVATIVES AS CANNABINOID RECEPTOR MODULATORS

(75) Inventors: Josephus H. M. Lange, Weesp (NL); Cornelis G. Kruse, Weesp (NL); Herman H. Van Stuivenberg, Weesp (NL); Hiskias G. Keizer, Weesp (NL)

(73) Assignee: Solvay Pharmaceuticals, Inc.

( * ) Notice: Subject to any disclaimer, the term of this patent is extended or adjusted under 35 U.S.C. 154(b) by 0 days.

(21) Appl. No.: 11/842,657

(22) Filed: Aug. 21, 2007

(65) Prior Publication Data

US 2007/0281974 A1    Dec. 6, 2007

Related U.S. Application Data

(62) Division of application No. 10/965,155, filed on Oct. 15, 2004, now Pat. No. 7,271,189.

(60) Provisional application No. 60/512,105, filed on Oct. 20, 2003.

(51) Int. Cl.
  A61K 31/4523  (2006.01)
  A61K 31/4178  (2006.01)
  A61K 31/4166  (2006.01)
(52) U.S. Cl. .................. 514/326; 514/397; 514/400
(58) Field of Classification Search ............. 514/326, 514/397, 400
  See application file for complete search history.

(56) References Cited

U.S. PATENT DOCUMENTS 7,186,734 B2 *   3/2007  Maynard et al. ............ 514/341
2004/0214855 A1  10/2004  Carpino et al.
2005/0026983 A1   2/2005  Carpino
2006/0128673 A1 * 6/2006  Firnges et al. ............. 514/149

OTHER PUBLICATIONS

Lange, et al. "Medicinal chemistry strategies to CB1 cannabinoid receptor antagonists", Drug Discovery Today, vol. 10(10), pp. 693-702, 695 (May 2005).*

* cited by examiner

*Primary Examiner*—Kamal A Saeed
*Assistant Examiner*—Kristin Bianchi
(74) *Attorney, Agent, or Firm*—Finnegan, Henderson, Farabow, Garrett & Dunner, LLP

(57) ABSTRACT

The invention relates to a group of 1H-imidazole derivatives which are modulators of cannabinoid receptors, to methods for the preparation of these compounds, to novel intermediates useful for the synthesis of said imidazole derivatives, to methods for the preparation of these intermediates, to pharmaceutical compositions containing one or more of these 1H-imidazole derivatives as active ingredient, as well as to the use of these pharmaceutical compositions for the treatment of psychiatric and neurological disorders in which cannabinoid receptors are involved.

The compounds have the general formula (I)

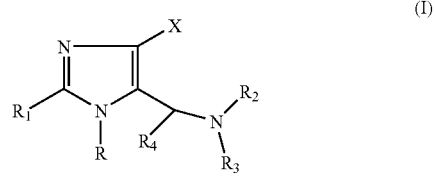

wherein R, $R_1$-$R_4$ and X have the meanings given in the specification.

3 Claims, No Drawings

1H-IMIDAZOLE DERIVATIVES AS CANNABINOID RECEPTOR MODULATORS

This is a division of application Ser. No. 10/965,155, filed Oct. 15, 2004 now U.S. Pat. No. 7,271,189, which claims benefit of U.S. Provisional Application No. 60/512,105, filed Oct. 20, 2003, the disclosures of both of which are incorporated herein by reference.

The present invention relates to a group of 1H-imidazole derivatives which are modulators of cannabinoid receptors, to methods for the preparation of these compounds, to novel intermediates useful for the synthesis of said imidazole derivatives, to methods for the preparation of these intermediates, to pharmaceutical compositions containing one or more of these 1H-imidazole derivatives as active ingredient, as well as to the use of these pharmaceutical compositions for the treatment of psychiatric and neurological disorders in which cannabinoid receptors are involved.

The invention also relates to the use of a compound disclosed herein for the manufacture of a medicament giving a beneficial effect. A beneficial effect is disclosed herein or apparent to a person skilled in the art from the specification and general knowledge in the art.

The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament.

1H-Imidazole derivatives as $CB_1$ receptor modulators are already known from WO 03/027076. However, the compounds described in WO 03/027076 are characterized by a relatively poor aqueous solubility. The goal of the present invention was to improve the aqueous solubility of 1H-imidazole derivatives whilst maintaining their cannabinoid receptor modulating activity. From the prior art it is not obvious how this goal should be achieved.

Surprisingly, it has now been found that the introduction of a 5-aminomethyl moiety in the 1H-imidazole core results in an enhanced aqueous solubility. Moreover, the derivatives containing said 5-aminomethyl moiety retain their cannabinoid receptor modulating activity, such as receptor antagonism, receptor inverse agonism or receptor (partial) agonism.

The invention relates to compounds of the general formula (I)

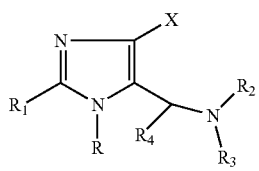

(I)

wherein:
R and $R_1$ are the same or different and represent phenyl, thienyl, pyridinyl, pyrimidinyl, pyrazinyl, pyridazinyl or triazinyl, which groups may be substituted with 1, 2, 3 or 4 substituents Y, which can be the same or different, selected from the group consisting of methyl, ethyl, propyl, methoxy, ethoxy, hydroxy, hydroxymethyl, hydroxyethyl, chloro, iodo, bromo, fluoro, trifluoromethyl, trifluoromethoxy, methylsulfonyl, phenyl and cyano, or R represents naphtyl, or R represents a $C_{1-8}$ branched or linear alkyl group, a $C_{3-7}$ cycloalkyl group, $C_{3-7}$ cycloalkyl-$C_{1-2}$ alkyl group, a $C_{3-8}$ branched or linear heteroalkyl group, a $C_{5-7}$ heterocycloalkyl group or a $C_{5-7}$ heterocycloalkyl-$C_{1-2}$ alkyl group which groups may be substituted with a fluoro atom or a $CF_3$ or OH group, $R_2$ and $R_3$ are the same or different and represent H, a $C_{1-5}$ branched or linear alkyl group which alkyl group may be substituted with a hydroxy group, or 1-3 fluoro atoms or, $R_2$ represents a branched or linear $C_{1-3}$ alkoxy group, with the proviso that $R_3$ represents H or a methyl group $R_2$ and $R_3$—together with the nitrogen atom to which they are bonded—form a saturated or unsaturated non-aromatic, monocyclic or bicyclic, heterocyclic group having 5 to 10 ring atoms which heterocyclic group contains one or two ring heteroatoms from the group (N, O, S), which heteroatoms can be the same or different, which heterocyclic group may be substituted with a $C_{1-3}$ alkyl group, a hydroxy group, or a fluoro atom, $R_4$ represents H or a methyl, ethyl, propyl, isopropyl or n-butyl group, X represents one of the subgroups (i), or (ii),

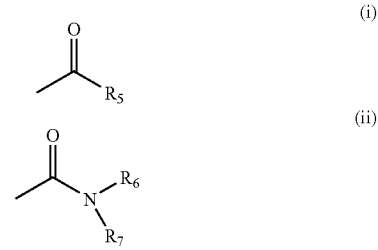

wherein:
$R_5$ represents a hydrogen atom, or a $C_{1-8}$ branched or linear alkyl group, $C_{1-3}$-alkyl-$SO_2$-$C_{1-4}$-alkyl group, $C_{3-7}$ cycloalkyl group, $C_{3-7}$-cycloalkyl-$C_{1-2}$-alkyl group, $C_{5-7}$-heterocycloalkyl-$C_{1-2}$-alkyl group which groups may be substituted with a hydroxy, methyl or trifluoromethyl group or a fluoro atom and which $C_{5-7}$-heterocycloalkyl-$C_{1-2}$-alkyl group contains one or two heteroatoms from the group (O, N, S), or $R_5$ represents a phenyl, benzyl, phenethyl or phenylpropyl group which may be substituted on their phenyl ring with 1-3 substituents Y, wherein Y has the abovementioned meaning, or $R_5$ represents a pyridyl or thienyl group, $R_6$ represents a hydrogen atom or a branched or linear $C_{1-3}$ alkyl group, $R_7$ represents hydrogen, a branched or linear $C_{1-8}$ alkyl or $C_{3-8}$-cycloalkyl-$C_{1-2}$-alkyl group, branched or linear $C_{1-8}$ alkoxy, $C_{3-8}$ cycloalkyl, $C_{5-10}$ bicycloalkyl, $C_{5-10}$ bicycloalkyl-$C_{1-2}$ alkyl, $C_{6-10}$ tricycloalkyl, $C_{6-10}$ tricycloalkylmethyl, which groups may contain one or more heteroatoms from the group (O, N, S) and which groups may be substituted with a hydroxy group, 1-3 methyl groups, an ethyl group or 1-3 fluoro atoms, or $R_7$ represents a phenyl, phenylamino, phenoxy, benzyl, phenethyl or phenylpropyl group, optionally substituted on their phenyl ring with 1-3 substituents Y, wherein Y has the abovementioned meaning, or $R_7$ represents a pyridyl or thienyl group, or $R_7$ represents a group $NR_8R_9$ wherein $R_8$ and $R_9$—together with the nitrogen atom to which they are attached-form a saturated or unsaturated, monocyclic or bicyclic, heterocyclic group having 4 to 10 ring atoms, which heterocyclic group contains one or more heteroatoms from the group (O, N, S) and which heterocyclic group may be substituted with a branched or linear $C_{1-3}$ alkyl, phenyl, hydroxy or trifluoromethyl group or a fluoro atom, or $R_6$ and $R_7$—together with the nitrogen atom to which they are attached—form a saturated or unsaturated, monocyclic or bicyclic, heterocyclic group having 4 to 10 ring atoms, which heterocyclic group contains one or more heteroatoms from the group (O, N, S) and which heterocyclic group may be substituted with a branched or linear $C_{1-3}$ alkyl, phenyl, amino, hydroxy or trifluoromethyl group or a fluoro atom, and pharmacologically acceptable salts and prodrugs thereof.

To the invention belong all compounds having formula (I), racemates, mixtures of diastereomers and the individual stereoisomers. Thus compounds in which the substituents on potentially asymmetrical carbon atoms are in either the R-configuration or the S-configuration belong to the invention.

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", Expert Opin. Ther. Patents, 14(3), 277-280, 2004; P. Ettmayer et al., "Lessons learned from marketed and investigational prodrugs", J. Med. Chem., 47, 2393-2404, 2004). Pro-drugs, i.e. compounds which when administered to humans by any known route, are metabolised to compounds having formula (I), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxylmethylene derivative, an O-(acyloxy-methylene carbamate) derivative, carbamate, ester, amide or enaminone.

The invention particularly relates to compounds having formula (I) wherein X represents the subgroup (ii), and all other symbols have the meanings as described above.

More particular the invention relates to compounds of formula (I) wherein X represents the subgroup (ii), and R represents phenyl, thienyl, pyridinyl, pyrimidinyl, pyrazinyl, pyridazinyl or triazinyl, which groups may be substituted with 1, 2, 3 or 4 substituents Y, which can be the same or different, from the group methyl, ethyl, propyl, methoxy, ethoxy, hydroxy, hydroxymethyl, hydroxyethyl, chloro, iodo, bromo, fluoro, trifluoromethyl, trifluoromethoxy, methylsulfonyl, phenyl or cyano, or R represents naphtyl, and all other symbols have the meanings as described above.

General Aspects of Syntheses

Compounds of formula (I) and the synthetic intermediates of formula (II) and (VI) respectively may be prepared by a variety of methodologies. The synthesis of structurally related imidazoles as cannabinoid receptor modulators has been described in WO 03/027076 and WO 03/063781. The synthesis of structurally related imidazoles as anti-obesity compounds has also been described in WO 03/040107. The selection of the particular method depends on factors such as the compatibility of functional groups with the reagents used, the possibility to use protecting groups, catalysts, activating and coupling reagents and the ultimate structural features present in the final compound being prepared. More information on activating and coupling methods of amines to carboxylic acids can be found in:

a) M. Bodanszky and A. Bodanszky: *The Practice of Peptide Synthesis*, Springer-Verlag, New York, 1994; ISBN: 0-387-57505-7;

b) K. Akaji et al., *Tetrahedron Lett.*, 1994, 35, 3315-3318);

c) F. Albericio et al., *Tetrahedron Lett.*, 1997, 38, 4853-4856).

More information on trimethylaluminum $Al(CH_3)_3$ promoted amidation reactions of esters can be found in: J. I. Levin, E. Turos, S. M. Weinreb, *Synth Commun.* 1982, 12, 989-993.). For more information on nucleophiles, electrophiles and the leaving group concept see: M. B. Smith and J. March: Advanced organic chemistry, p. 275, $5^{th}$ ed., (2001) John Wiley & Sons, New York, ISBN: 0-471-58589-0). More information on addition and subsequent removal of protective groups in organic synthesis can be found in: T. W. Greene and P. G. M. Wuts, "Protective Groups in Organic Synthesis", third edition, John Wiley & Sons, Inc., New York, 1999.

A suitable synthesis for the compounds of the invention is the following:

Synthesis Route A

Reaction of a compound having formula (II)

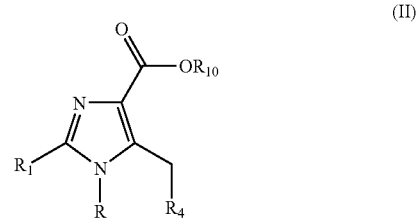

(II)

wherein R, $R_1$, $R_4$ have the meanings given above and $R_{10}$ represents a branched or linear alkyl group ($C_{1-4}$) or benzyl group with a regioselective brominating compound such as N-bromosuccinimide (NBS) in an organic solvent such as $CCl_4$ in the presence of a free-radical initiator such as dibenzoyl peroxide can give a compound of formula (III)

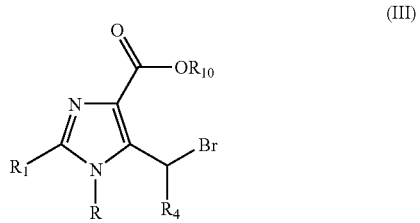

(III)

wherein R, $R_1$, $R_4$ and $R_{10}$ have the meanings given above. Reaction of a compound having formula (III) with an amine of general formula $R_2R_3NH$ can give a compound of general formula (IV)

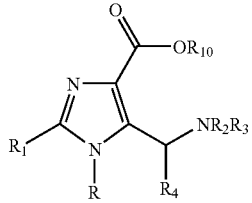

wherein R, $R_1$, $R_2$, $R_3$, $R_4$ and $R_{10}$ have the meanings given above.

Compounds of general formula (IV) which have been obtained according to synthesis route A can be converted to compounds of general formula (I) wherein X represents subgroup (ii), analogously to the procedures described in WO 03/027076.

Synthesis Route B

Reaction of a compound having formula (IV) wherein R, $R_1$, $R_2$, $R_3$ and $R_4$ have the meanings given above and $R_{10}$ represents a hydrogen atom

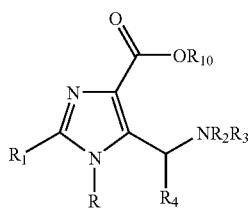

with N-methoxy-N-methylamine can give a compound of formula (V),

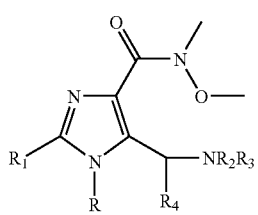

wherein R, $R_1$, $R_2$, $R_3$ and $R_4$ have the meanings given above. Reaction of a compound having formula (V) with an organo-metallic compound of general formula $R_5$—MgBr (a Grignard reagent) or $R_5$—Li (an organo-lithium reagent) can give a compound of general formula (I), wherein X represents subgroup (i). Such a reaction is preferably carried out under $N_2$ in an anhydrous inert organic solvent.

Synthesis Route C

2-Aryl-(1H)-imidazole-4-carboxylates can be obtained according to the procedure described in *Tetrahedron Lett.* (1971), 18, 1439-1440 (Heindel and Chun). Subsequent derivatisation (for example, an N-arylation or N-alkylation reaction) of the proper imidazole N-atom can produce compounds having formula (VI). Reaction of a compound having formula (VI)

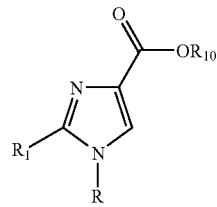

wherein R and $R_1$ have the meanings given above and $R_{10}$ represents a branched or linear alkyl group ($C_{1-4}$) or benzyl group, with a non-nucleophilic base such as lithium diisopropylamide (LDA), followed by an electrophile such as formic acid ethyl ester in an inert anhydrous organic solvent such as THF can give a compound of general formula (VII)

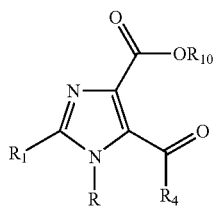

wherein R, $R_1$, $R_4$ and $R_{10}$ have the meanings given above in this synthetic route. Reductive amination of a compound having general formula (VII) with an amine of general formula $R_2R_3NH$ in the presence of a reducing agent such as $NaCNBH_3$ can give a compound of general formula (IV)

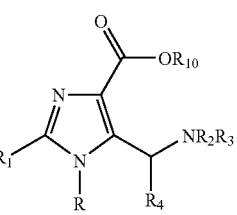

wherein R, $R_1$, $R_2$, $R_3$, $R_4$ and $R_{10}$ have the meanings given above in this synthetic route.

Compounds of general formula (IV) which have been obtained according to synthesis route C can be converted to compounds of general formula (I) wherein X represents subgroup (ii), analogously to the procedures described in WO 03/027076.

Pharmaceutically acceptable salts may be obtained using standard procedures well known in the art, for example by mixing a compound of the present invention with a suitable acid, for instance an inorganic acid such as hydrochloric acid, or with an organic acid.

Due to their cannabinoid receptor modulating activity the compounds according to the invention are suitable for use in the treatment of psychiatric disorders such as psychosis, anxiety, depression, attention deficits, memory disorders, cognitive disorders, appetite disorders, obesity, in particular juvenile obesity and drug induced obesity, addiction, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, sexual disorders, liver cirrhosis, gastric ulcers, diarrhoea and cardiovascular disorders.

The cannabinoid receptor modulating activity of the compounds of the invention makes them particularly useful in the treatment of obesity, juvenile obesity and drug induced obesity, when used in combination with lipase inhibitors. Specific examples of compounds which can be used in such combination preparations are (but not restricted to) the synthetic lipase inhibitor orlistat, lipase inhibitors isolated from micro organisms such as lipstatin (from *Streptomyces toxytricini*), ebelactone B (from *Streptomyces aburaviensis*), synthetic derivatives of these compounds, as well as extracts of plants known to possess lipase inhibitory activity, for instance extracts of *Alpinia officinarum* or compounds isolated from such extracts like 3-methylethergalangin (from *A. officinarum*).

The compounds of the invention can be brought into forms suitable for administration by means of usual processes using auxiliary substances and/or liquid or solid carrier materials.

Compounds of the invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In Vitro Affinity for Cannabinoid-$CB_1$ Receptors

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In vitro Affinity for Cannabinoid-$CB_2$ Receptors

The affinity of the compounds of the invention for cannabinoid $CB_2$ receptors can be determined using membrane preparations of Chinese hamster ovary (CHO) cells in which the human cannabinoid $CB_2$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In vitro Cannabinoid-$CB_1$ Receptor Antagonism

In vitro $CB_1$ receptor antagonism can be assessed with the human $CB_1$ receptor cloned in Chinese hamster ovary (CHO) cells. CHO cells are grown in a Dulbecco's Modified Eagle's medium (DMEM) culture medium, supplemented with 10% heat-inactivated fetal calf serum. Medium is aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid is incorporated in membrane phospholipids. On the test day, medium is aspirated and cells are washed three times using 0.5 mL DMEM, containing 0.2% bovine serum albumin (BSA). Stimulation of the $CB_1$ receptor by WIN 55,212-2 leads to activation of $PLA_2$ followed by release of [$^3$H]-arachidonic acid into the medium. This WIN 55,212-2-induced release is concentration-dependently antagonized by $CB_1$ receptor antagonists.

In vivo Cannabinoid-$CB_1$ Receptor Antagonism

In vivo $CB_1$ antagonism can be assessed with the CP-55,940-induced hypotension test in rat. Male normotensive rats (225-300 g; Harlan, Horst, The Netherlands) are anaesthetized with pentobarbital (80 mg/kg ip). Blood pressure is measured, via a cannula inserted into the left carotid artery, by means of a Spectramed DTX-plus pressure transducer (Spectramed B. V., Bilthoven, The Netherlands). After amplification by a Nihon Kohden Carrier Amplifier (Type AP-621G; Nihon Kohden B. V., Amsterdam, The Netherlands), the blood pressure signal is registered on a personal computer (Compaq Deskpro 386s), by means of a Po-Ne-Mah data-acquisition program (Po-Ne-Mah Inc., Storrs, USA). Heart rate is derived from the pulsatile pressure signal. All compounds are administered orally as a microsuspension in 1% methylcellulose 30 minutes before induction of the anesthesia which is 60 minutes prior to administration of the $CB_1$ receptor agonist CP-55,940. The injection volume is 10 ml/kg. After haemodynamic stabilization the $CB_1$ receptor agonist CP-55,940 (0.1 mg/kg i.v.) is administered and the hypotensive effect established. (Wagner, J. A.; Jarai, Z.; Batkai, S.; Kunos, G. Hemodynamic effects of cannabinoids: coronary and cerebral vasodilation mediated by cannabinoid CB1 receptors. *Eur. J. Pharmacol.* 2001, 423, 203-210); Lange, J. H. M. et al., *J. Med. Chem.* 2004, 47, 627-643.

In vivo Cannabinoid-$CB_1$ Receptor (Partial) Agonistic Activity

Cannabinoid receptor agonistic or partial agonistic activity of compounds of the invention can be determined according to published methods, such as assessment of in vivo cannabimimetic effects (Wiley, J. L. et al., *J. Pharmacol. Exp. Ther.* 2001, 296, 1013).

Determination of Aqueous Solubility

The compounds are dissolved in DMSO to give 10 mg/ml stock solutions. These stock solutions are divided over several plates. Several diluted concentrations are made with DMSO to 5, 2.5, 1.25, 0.625 and 0.3125 mg/ml, respectively. The stock solution and each derived concentration from this stock solution is taken and diluted 100 fold with water or with water containing a buffer. In every case this gives an aqueous solution which contains 1% DMSO (v/v) and 100, 50, 25, 12.5 and 6.25 and 3.125 µg compound/ml, respectively. The formation of a precipitate is determined in each plate. The measurements were performed at pH=7, applying a HEPES buffer and at pH=2, applying hydrochloric acid. Aqueous solubility is expressed in µg/ml in the table below.

EXAMPLE 1

Syntheses of Specific Compounds

Synthesis of Compound 1

Part A: Ethyl 5-bromomethyl-1-(4-chlorophenyl)-2-(2,4-dichlorophenyl)-1H-imidazole-4-carboxylate. To a magnetically stirred mixture of ethyl 1-(4-chlorophenyl)-2-(2,4-dichlorophenyl)-5-methyl-1H-imidazole-4-carboxylate (2.05 g, 5.00 mmol) in CCl$_4$ (25 mL) was added N-bromosuccinimide (NBS) (1.34 g, 7.53 mmol) and dibenzoyl peroxide (10.0 mg, assay 75%, 0.0310 mmol) and the resulting mixture was refluxed for 38 h. The formed precipitate was removed by filtration. The filtrate was successively washed with brine and water, dried over MgSO$_4$, filtered and concentrated in vacuo. The residue was purified by flash chromatography (CH$_2$Cl$_2$/acetone=98/2 (v/v)) to give ethyl 5-bromomethyl-1-(4-chlorophenyl)-2-(2,4-dichlorophenyl)-1H-imidazole-4-carboxylate (1.29 g, 53% yield) as an amorphous solid, $^1$H-NMR (200 MHz, CDCl$_3$): δ 1.45 (t, J=7 Hz, 3H), 4.48 (q, J=7 Hz, 2H), 4.72 (s, 2H), 7.18-7.43 (m, 7H).

Part B: To a magnetically stirred solution of ethyl 5-bromomethyl-1-(4-chlorophenyl)-2-(2,4-dichlorophenyl)-1H-imidazole-4-carboxylate (11.69 g, 23.9 mmol) in acetonitrile (40 ml) is added diisopropylethylamine (DIPEA) (5.2 ml, 30 mmol) and pyrrolidine (1.7 g, 23.9 mmol) and the resulting solution is reacted at room temperature for 2 hours. Water (250 ml) is added and the resulting mixture is extracted three times with dichloromethane. The collected dichloromethane layers are dried over Na$_2$SO$_4$, filtered and concentrated in vacuo. Subsequent purification with flash chromatography (petroleum ether/EtOAc=20/80 (v/v)) gives ethyl 1-(4-chlorophenyl)-2-(2,4-dichloro-phenyl)-5-(pyrrolidin-1-ylmethyl)-1H-imidazole-4-carboxylate (3.7 gram, 32% yield). $^1$H-NMR (200 MHz, CDCl$_3$): δ 1.42 (t, J=7 Hz, 3H), 1.62-1.72 (m, 4H), 2.42-2.50 (m, 4H), 3.83 (s, 2H), 4.43 (q, J=7 Hz, 2H), 7.17-7.40 (m, 7H).

Part C: Cyclohexylamine (0.91 ml, 8 mmol) is dissolved in dichloromethane (20 ml) and (CH$_3$)$_3$Al (4 ml of a 2 M solution in heptane, 8 mmol) is added. The resulting mixture is stirred for 10 minutes at room temperature and ethyl 1-(4-chlorophenyl)-2-(2,4-dichlorophenyl)-5-(pyrrolidin-1-ylmethyl)-1H-imidazole-4-carboxylate (1.8 gram, 3.8 mmol) is added. The resulting mixture is stirred at room temperature for 16 hours, poured into an aqueous NaHCO$_3$ solution, stirred for 30 minutes and filtered over hyflo. The filtrated is twice extracted with dichloromethane. The organic layers are dried over Na$_2$SO$_4$, filtered and concentrated in vacuo. Subsequent purification with flash chromatography (dichloromethanelmethanol=98/2 (v/v)) gives N-cyclohexyl-1-(4-chlorophenyl)-2-(2,4-dichlorophenyl)-5-(pyrrolidin-1-ylmethyl)-1H-imidazole-4-carboxamide, compound 1 (1.06 gram, 53% yield). Melting point: 155-157° C.

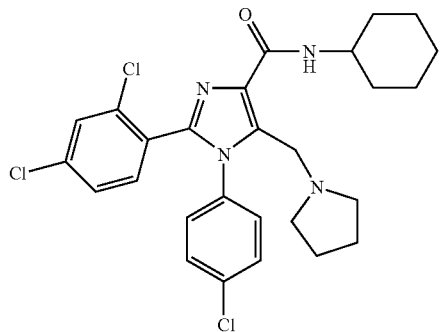

Analogously, the following compounds 2-6 were prepared:
2. N-cyclohexyl-1-(4-chlorophenyl)-2-(2,4-dichlorophenyl)-5-(N-ethyl,N-methylaminomethyl)-1H-imidazole-4-carboxamide. Melting point: 135-136° C.

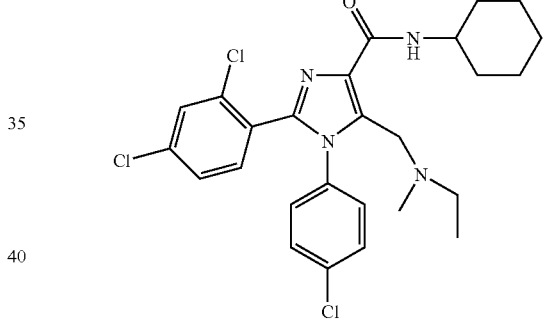

3. N-(piperidin-1-yl)-1-(4-chlorophenyl)-2-(2,4-dichlorophenyl)-5-(N,N-dimethylaminomethyl)-1H-imidazole-4-carboxamide. Melting point: 163-166° C.

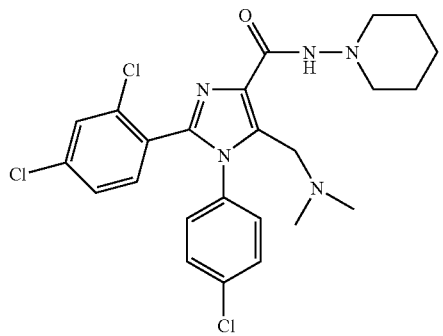

4. N-cyclohexyl-1-(4-chlorophenyl)-2-(2,4-dichlorophenyl)-5-(N,N-dimethylaminomethyl)-1H-imidazole-4-carboxamide. ¹H-NMR (400 MHz, CDCl₃): δ 1.12-1.68 (m, 6H), 1.72-1.80 (m, 2H), 1.99-2.06 (m, 2H), 2.18 (s, 6H), 3.65 (s, 2H), 3.88-4.00 (m, 1H), 7.22-7.37 (m, 8H).

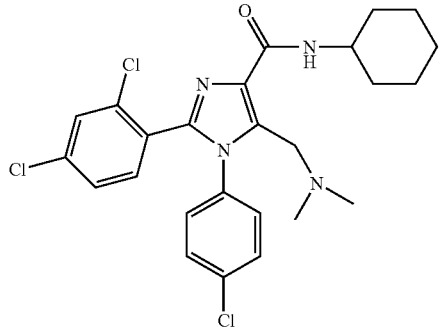

5. N-(piperidin-1-yl)-1-(4-chlorophenyl)-2-(2,4-dichlorophenyl)-5-(pyrrolidin-1-ylmethyl)-1H-imidazole-4-carboxamide. 2 HCl. ¹H-NMR (400 MHz, DMSO-d₆): δ 1.46-1.56 (m, 2H), 1.79-1.96 (m, 8H), 2.90-3.00 (m, 2H), 3.26-3.50 (m, 6H), 4.57 (br s, 2H), 7.45-7.60 (m, 6H), 7.70 (d, J=8 Hz, 1H), 10.95 (br s, 2H).

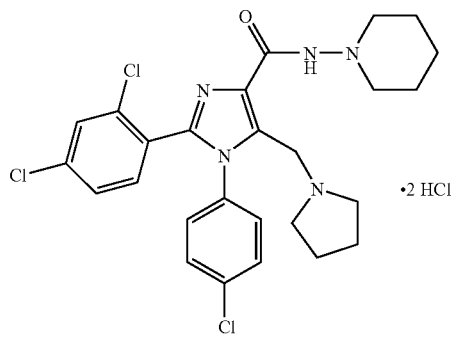

6. N-(piperidin-1-yl)-1-(4-chlorophenyl)-2-(2,4-dichlorophenyl)-5-(N-ethyl, N-methylaminomethyl)-1H-imidazole-4-carboxamide. ¹H-NMR (400 MHz, CDCl₃): δ 0.86 (t, J=7 Hz, 3H), 1.38-1.46 (m, 2H), 1.72-1.78 (m, 4H), 2.14 (s, 3H), 2.36 (q, J=7 Hz, 2H), 2.82-2.86 (m, 4H), 3.72 (s, 2H), 7.21-7.31 (m, 6H), 7.34 (d, J=2 Hz, 1H), 8.16 (br s, 1H).

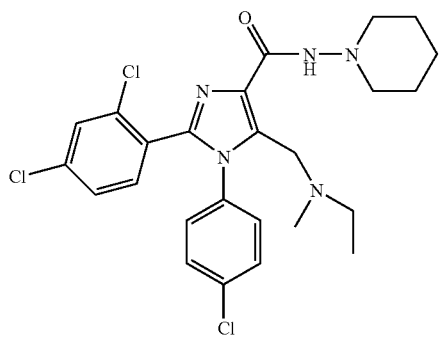

EXAMPLE 2

Determination of Aqueous Solubilities

Aqueous solubilities of two of the compounds of general formula (I), the compounds 1 and 4, and the compound 1-(4-chlorophenyl)-2-(2,4-dichloro-phenyl)-N-cyclohexyl-1H-imidazole-4-carboxamide (compound 3 from WO 03/063781) were determined according to the procedure described above. The results are shown in Table 1.

TABLE 1

| aqueous solubility (expressed in µg/ml) | | |
|---|---|---|
| | | Aqueous solubility in µg/ml at: |
| Compound name | pH = 2 | pH = 7 |
| N-cyclohexyl-1-(4-chlorophenyl)-2-(2,4-dichlorophenyl)-5-(pyrrolidin-1-ylmethyl)-1H-imidazole-4-carboxamide (compound 1) | >100 | 50 |
| N-cyclohexyl-1-(4-chlorophenyl)-2-(2,4-dichlorophenyl)-5-(N,N-dimethylaminomethyl)-1H-imidazole-4-carboxamide (compound 4) | >100 | 50 |
| N-cyclohexyl-1-(4-chlorophenyl)-2-(2,4-dichlorophenyl)-1H-imidazole-4-carboxamide (WO 03/063781) | 25 | 25 |

EXAMPLE 3

Pharmacological Data

Pharmacological test results of a subset of the compounds of the invention, obtained with the assay described above, are given in table 2 below:

TABLE 2

| pharmacological data | |
|---|---|
| Compound | Human cannabinoid-CB₁ receptor In vitro affinity - pK$_i$ value |
| Compound 1 | 8.1 |
| Compound 2 | 8.2 |
| Compound 3 | 7.0 |
| Compound 4 | 7.5 |
| Compound 5 | 6.3 |
| Compound 6 | 6.9 |

The invention claimed is:

1. A method for treating at least one disorder involving cannabinoid neurotransmission in a human patient in need of such treatment, wherein said at least one disorder is chosen from psychosis, anxiety, depression, attention deficit disorders, and appetite disorders, said method comprising administering to said human patient a pharmaceutical composition comprising at least one pharmacologically active compound of formula (I)

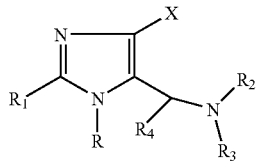

(I)

or a stereoisomer thereof, or a pharmacologically acceptable salt or prodrug thereof, wherein:

R and $R_1$ are the same or different and represent phenyl, thienyl, pyridinyl, pyrimidinyl, pyrazinyl, pyridazinyl or triazinyl, which groups may be substituted with 1, 2, 3 or 4 substituents Y, which can be the same or different and are chosen from methyl, ethyl, propyl, methoxy, ethoxy, hydroxy, hydroxymethyl, hydroxyethyl, chloro, iodo, bromo, fluoro, trifluoromethyl, trifluoromethoxy, methylsulfonyl, phenyl and cyano; or R represents naphtyl;

or R represents a $C_{1-8}$ branched or linear alkyl group, a $C_{3-7}$ cycloalkyl group, a $C_{3-7}$ cycloalkyl-$C_{1-2}$ alkyl group, a $C_{3-8}$ branched or linear heteroalkyl group, a $C_{5-7}$ heterocycloalkyl group or a $C_{5-7}$ heterocycloalkyl-$C_{1-2}$ alkyl group, which groups may be substituted with a fluoro atom or a $CF_3$ or OH group;

$R_2$ and $R_3$ are the same or different and represent H, a $C_{1-5}$ branched or linear alkyl group, which alkyl group may be substituted with a hydroxy group, or 1-3 fluoro atoms; or $R_2$ represents a branched or linear $C_{1-3}$ alkoxy group, with the proviso that $R_3$ represents H or a methyl group; or $R_2$ and $R_3$, together with the nitrogen atom to which they are bonded, form a saturated or unsaturated non-aromatic, monocyclic or bicyclic, heterocyclic group having 5 to 10 ring atoms, which heterocyclic group contains one or two ring heteroatoms chosen from the group (N, O, S), which heteroatoms can be the same or different, and which heterocyclic group may be substituted with a $C_{1-3}$ alkyl group, a hydroxy group, or a fluoro atom;

$R_4$ represents H or a methyl, ethyl, propyl, isopropyl or n-butyl group;

X represents one of (i), or (ii),

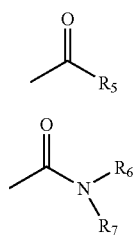

wherein:

$R_5$ represents a hydrogen atom, or a $C_{1-8}$ branched or linear alkyl group, $C_{1-3}$-alkyl-$SO_2$—$C_{1-4}$-alkyl group, $C_{3-7}$ cycloalkyl group, $C_{3-7}$-cycloalkyl-$C_{1-2}$-alkyl group, or $C_{5-7}$-heterocycloalkyl-$C_{1-2}$-alkyl group, which groups may be substituted with a hydroxy, methyl or trifluoromethyl group or a fluoro atom, and which $C_{5-7}$-heterocycloalkyl-$C_{1-2}$-alkyl group contains one or two heteroatoms chosen from the group (O, N, S); or $R_5$ represents a phenyl, benzyl, phenethyl or phenylpropyl group which may be each substituted on their phenyl ring with 1-3 substituents Y, wherein Y has the above mentioned meaning; or $R_5$ represents a pyridyl or thienyl group;

$R_6$ represents a hydrogen atom or a branched or linear $C_{1-3}$ alkyl group;

$R_7$ represents hydrogen, a branched or linear $C_{1-8}$ alkyl or $C_{3-8}$-cycloalkyl-$C_{1-2}$-alkyl group, a branched or linear $C_{1-8}$ alkoxy, $C_{3-8}$ cycloalkyl, $C_{5-10}$ bicycloalkyl, $C_{5-10}$ bicycloalkyl-$C_{1-2}$ alkyl, $C_{6-10}$ tricycloalkyl, or $C_{6-10}$ tricycloalkylmethyl group, which groups may contain one or more heteroatoms chosen from the group (O, N, S) and which groups may be substituted with one or more substituents chosen from a hydroxy group, from 1 to 3 methyl groups, an ethyl group or from 1 to 3 fluoro atoms; or $R_7$ represents a phenyl, phenylamino, phenoxy, benzyl, phenethyl or phenylpropyl group, optionally substituted on their phenyl ring with 1 to 3 substituents Y, wherein Y has the abovementioned meaning; or $R_7$ represents a pyridyl or thienyl group; or $R_7$ represents a group $NR_8R_9$, wherein $R_8$ and $R_9$, together with the nitrogen atom to which they are attached form a saturated or unsaturated, monocyclic or bicyclic, heterocyclic group having from 4 to 10 ring atoms, which heterocyclic group contains one or more heteroatoms chosen from the group (O, N, S) and which heterocyclic group may be substituted with a branched or linear $C_{1-3}$ alkyl, phenyl, hydroxy or trifluoromethyl group or a fluoro atom; or $R_6$ and $R_7$, together with the nitrogen atom to which they are attached, form a saturated or unsaturated, monocyclic or bicyclic, heterocyclic group having 4 to 10 ring atoms, which heterocyclic group contains one or more heteroatoms chosen from the group (O, N, S) and which heterocyclic group may be substituted with a branched or linear $C_{1-3}$ alkyl, phenyl, amino, hydroxy or trifluoromethyl group or a fluoro atom.

2. The method of claim 1, wherein the pharmaceutical composition further comprises at least one lipase inhibitor.

3. The method of claim 2, wherein the at least one lipase inhibitor is orlistat or lipstatin.

* * * * *

UNITED STATES PATENT AND TRADEMARK OFFICE
CERTIFICATE OF CORRECTION

PATENT NO.      : 7,498,348 B2
APPLICATION NO. : 11/842657
DATED           : March 3, 2009
INVENTOR(S)     : Lange et al.

Page 1 of 1

It is certified that error appears in the above-identified patent and that said Letters Patent is hereby corrected as shown below:

Claim 1 col. 13, line 16, "chioro" should read --chloro--.

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,498,348 B2  Page 1 of 1
APPLICATION NO. : 11/842657
DATED : March 3, 2009
INVENTOR(S) : Lange et al.

It is certified that error appears in the above-identified patent and that said Letters Patent is hereby corrected as shown below:

Title page, item (73) "Assignee: Solvay Pharmaceuticals, Inc." should read --Assignee: Solvay Pharmaceuticals, B.V., Weesp (NL)--.

Claim 1 col. 13, line 16, "chioro" should read --chloro--.

Signed and Sealed this

Twenty-sixth Day of January, 2010

David J. Kappos
*Director of the United States Patent and Trademark Office*